United States Patent
Hsieh et al.

(10) Patent No.: US 7,142,636 B2
(45) Date of Patent: Nov. 28, 2006

(54) SYSTEM AND METHOD FOR DEFECTIVE DETECTOR CELL AND DAS CHANNEL CORRECTION

(75) Inventors: Jiang Hsieh, Brookfield, WI (US); Eugene Clifford Williams, Waukesha, WI (US)

(73) Assignee: General Electric Company, Schenectady, NY (US)

(*) Notice: Subject to any disclaimer, the term of this patent is extended or adjusted under 35 U.S.C. 154(b) by 325 days.

(21) Appl. No.: 10/668,444

(22) Filed: Sep. 23, 2003

(65) Prior Publication Data
US 2005/0063513 A1   Mar. 24, 2005

(51) Int. Cl.
*G01B 15/02* (2006.01)
(52) U.S. Cl. ......................... 378/98.8; 378/98
(58) Field of Classification Search ........... 382/275, 382/300, 132, 312, 514, 128; 250/370.09, 250/252.1; 348/246, 247; 378/98.8, 62, 378/98, 19
See application file for complete search history.

(56) References Cited

U.S. PATENT DOCUMENTS

| | | | |
|---|---|---|---|
| 6,118,846 A * | 9/2000 | Liu | 378/62 |
| 6,385,292 B1 | 5/2002 | Dunham et al. | |
| 2003/0001078 A1* | 1/2003 | Baharav et al. | 250/208.1 |
| 2005/0030394 A1* | 2/2005 | Mendis et al. | 348/246 |

FOREIGN PATENT DOCUMENTS

| | | | |
|---|---|---|---|
| JP | 11027523 A | * | 1/1999 |
| JP | 411027523 A | * | 1/1999 |

OTHER PUBLICATIONS

T.G. Riess, Q. Spreiter, T.O. Fuchs, T. Von der Haar, and W.A. Kalendar, "A fast and efficient method for the correction of defective channels in x-ray CT area detectors," Radiology 225(p), pp. 404, 2002.

* cited by examiner

*Primary Examiner*—Edward J. Glick
*Assistant Examiner*—Irakli Kiknadze
(74) *Attorney, Agent, or Firm*—McAndrews, Held & Malloy, Ltd.; Peter J. Vogel; Michael A. Dellapenna

(57) ABSTRACT

A method and system for an improved data acquisition system with an image detector array and an image processing system which finds a malfunctioning cell, interpolates a signal for the malfunctioning cell using neighboring channels of the cell, and corrects the interpolation with an error rate found in performing interpolations on neighboring rows with cells which are not malfunctioning. The image processing system may include a DAS and a reconstruction system. The step of finding a malfunctioning cell may be accomplished through a variety of methods, such as measuring discrepancies between a cell's and its neighboring cell's average readings over time and exposing the cells to x-rays which should produce similar readings in all the cells and comparing the cells' signals, looking for discrepancies. The step of interpolating and the step of correcting may take into consideration cells within the same projection view as the malfunctioning cell.

21 Claims, 5 Drawing Sheets malfunctioning sample

SYSTEM AND METHOD FOR DEFECTIVE DETECTOR CELL AND DAS CHANNEL CORRECTION

RELATED APPLICATIONS

[Not Applicable]

FEDERALLY SPONSORED RESEARCH OR DEVELOPMENT

[Not Applicable]

MICROFICHE/COPYRIGHT REFERENCE

[Not Applicable]

BACKGROUND OF THE INVENTION

The present invention relates to imaging systems and the accuracy of the image displayed to the user. More specifically, the invention relates to dynamically predicting signals of malfunctioning cells or suspected malfunctioning cells in an array of sensing devices, by utilizing other known signals.

Medical diagnostic imaging systems encompass a variety of imaging modalities, such as planar x-rays, ultrasound, magnetic resonance (MR), electron beam tomography (EBT), positron emission tomography (PET), single photon emission computed tomography (SPECT), micro computed tomography, and macro computed tomography imaging systems, and the like. Medical diagnostic imaging systems generate images of an object, such as a patient, through exposure to an energy source, such as x-rays passing through a patient. A generated image may be used for many purposes. For instance, internal defects in an object may be detected. Additionally, changes in internal structure or alignment may be determined. Fluid flow within an object may also be represented. Furthermore, the image may show the presence or absence of components in an object. Information gained from medical diagnostic imaging has applications in many fields, including medicine and manufacturing.

A typical imaging system uses an array of cells to detect an object and then reconstruct and display the detected image. The array includes multiple detector rows. Each detector row includes multiple detector cells, with each detector cell connected to a different data acquisition system (DAS) channel. That is, a DAS channel may be mapped to a detector cell. Each detector cell generates a signal. A large volume array includes a large number of detector cells and DAS channels. As a number of detector cells and DAS channels increases, a probability of failure in a detector cell, DAS channel, or DAS application-specific integrated circuit (ASIC) failure increases. Additionally, as a number of detector cells and DAS channels increases, it would be desirable for components of the imaging system and detector array to become more integrated.

A problem in any one detector cell in either the detector or the DAS channel may cause artifacts in the reconstructed images. Cells with a problem in the detector and/or the DAS channel are called malfunctioning cells. Malfunctioning cells may malfunction in several different ways, such as malfunctioning intermittently, giving a signal that is a certain percentage less accurate than other cells' signals, generating a signal that is a percentage weaker than neighboring cells, and not functioning at all. Any inaccuracies or "artifacts" in the image produced by the imaging system or cells in the imaging system may result in actions taken by physicians, medical practitioners or other observers based on incorrect information.

Increasing the volume coverage of the arrays of cells allows users to image larger objects faster because one sweep of a larger array images more of an object. Increasing a volume coverage of an arrays of cells also images an object more accurately because less time elapses during the imaging process when fewer sweeps are used to image the object. With a continued pursuit of larger volume coverage, a number of detectors and DAS channels increases quickly. As a result, a probability of a malfunctioning cell increases. Replacement of a malfunctioning cell significantly increases the cost of a system. Replacing all failed components on a system with a large number of detector channels may not be economical. In addition, failed components interrupt the operation flow in a hospital. Thus, a system that minimizes image artifacts or significant degradation in image quality due to a malfunctioning cell would be highly desirable.

One method proposed to minimize an impact of a failed detector channel and/or DAS channel utilizes an algorithm which estimates missing projection samples based on neighboring good samples. For the convenience of discussion, assume a projection sample corresponding to detector row n and channel i is defective. A defect may be the result of either detector failure or DAS channel failure, for example. A projection sample for a channel may be denoted by $p_k(i, n)$, where k is a projection view index.

A malfunctioning cell, $p_k(i, n)$, is in channel i, detector row n and view index k. The malfunctioning cell, $p_k(i, n)$, may be estimated by performing linear or bilinear interpolation using neighboring signals. That is, $p_k(i, n)$ is estimated using the average of signals $p_k(i-1, n)$ and $p_k(i+1, n)$, the neighboring lower and higher channels, for linear interpolation. Alternatively, $p_k(i, n)$ may be estimated using the average of signals $p_k(i-1, n)$, $p_k(i+1, n)$, $p_k(i, n-1)$, and $p_k(i, n+1)$, the neighboring lower and higher channels and the neighboring upper and lower rows, for bilinear interpolation. Although the approaches of linear and bilinear interpolation have computational advantages, both approaches suffer from image artifacts. A more elaborate scheme was proposed in a paper by Tillman Riess, Quirin Spriter, Theobald Fuchs, Thomas von der Haar, and Willi Kalendar entitled "A Fast and Efficient Method for the Correction of Defective Channels in X-ray CT Area Detectors." The proposed scheme relies on an interpolation in a Sinogram space. That is, the missing projection sample, $p_k(i, n)$, is estimated based on the samples of $p_{k-1}(i-1, n)$, $p_{k-1}(i, n)$, and $p_{k-1}(i+1, n)$ taken in a projection view before k, the samples $p_k(i-1, n)$ and $p_k(i+1, n)$ taken in a then current projection, and the samples $p_{k+1}(i-1, n)$, $p_{k+1}(i, n)$, and $p_{k+1}(i+1, n)$ taken in a future projection k+1. An estimation of a sample for view k uses not only the previously collected views, but also the next view, k+1. That is, an image reconstructor may have to wait for the arrival of the future projection before the current projection may be corrected.

However, future projections may not be the same as current projections because time elapses between images and different imaging angles result in different errors in the image. Especially when taking images of arteries or other parts of the body which change rapidly, projection views in the future are not a reliable source to predict past images because the image may have changed between projection views. Different projection views use different angles from which a detector takes a measurement. A different angle entails that a view travel a different distance. Longer distances cause more inaccuracies in an image because when a view travels a longer distance, more interference results in the image. For these and other reasons, future and previous projection views are an unreliable source for a current projection view's signals. Although the approach proposed by Riess et al. further reduces image artifacts, residual artifacts still remain.

Therefore a need exists for an improved method of minimizing an impact of a malfunctioning cell by utilizing data within the same projection view.

BRIEF SUMMARY OF THE INVENTION

Certain embodiments of the present invention provide a method and system for minimizing an impact of a malfunctioning cell by using other signals within the malfunctioning cell's projection view to minimize the number of artifacts which may be observed. A detector row in an array may have a malfunctioning cell in a channel and a projection view. An estimate for a malfunctioning cell's missing projection sample may be interpolated using good samples from neighboring channels of the malfunctioning cell in the same projection view and detector row. Because readings at each channel from a detector row are likely to follow smoothly from one to the next, an interpolation of a signal of a malfunctioning cell using neighboring channels is likely to be an accurate estimate. A missing projection sample of the malfunctioning cell may then be calculated.

In an embodiment, to improve the accuracy of an interpolation of the malfunctioning cell's signal, a same method of interpolation is performed on at least one of a nearest pair of neighboring detector rows. The interpolation is performed on the pair of neighboring rows. In an embodiment, each member of the pair is an equal distance above or below the detector row with the malfunctioning cell. At least one of the rows includes a good cell. A good cell has a good signal in the same projection view and channel as the malfunctioning cell. A good signal is a signal from a cell that is not malfunctioning.

A differential signal may be calculated by subtracting a good signal of a good cell from an interpolated signal using a neighboring row. A weighted average of differential signals is calculated. The weighted average may be based on at least one of several factors, such as where the rows are positioned in the array, how many known samples are in each neighboring row with a good cell used in the calculation, the magnitude of the good cell's signal and interpolations of the good cell's signal, and similarities in measurements between the detector row with the malfunctioning cell and the neighboring detector rows with the good cells used in estimating the signal of the malfunctioning cell.

The estimate for the malfunctioning cell is then adjusted by subtracting from the estimate the weighted average of the differential signals to form a final estimate for the missing projection sample of the malfunctioning cell.

To find a malfunctioning cell, cells in a detector row may be exposed directly to x-rays without an attenuating object in between. Then, each cell may be compared to the cell's neighbors' readings to determine which cells are malfunctioning. Alternatively, by using an average reading (over all projection views for each channel), changes in average signals between adjacent cells may identify malfunctioning cells.

In an embodiment, a correction scheme is used to examine malfunctioning cells, channels, and/or application-specific integrated circuits (ASICs) related to the data acquisition system (DAS). DAS ASICs may be mapped to detector cells and/or channels to optimize opportunities for correction. Malfunctioning channels and/or ASICs may then be identified and correction applied to minimize errors.

DETAILED DESCRIPTION OF THE INVENTION

Certain embodiments of the present invention provide a system and method for correcting errors in detector cells, DAS channels, and/or DAS ASICs. Certain embodiments examine or "ride through" single cells and/or ASICs with a correction scheme. A DAS ASIC may be mapped to detector cells or channels to optimize opportunities for correction. Malfunctioning channels and/or ASICs may then be identified and correction applied.

For the purpose of illustration only, the following detailed description references a certain embodiment of a computed tomography (CT) imaging system. It is understood that the present invention may be used with other imaging systems (such as planar x-rays, ultrasound, magnetic resonance (MR), positron emission tomography (PET), single photon emission computed tomography (SPECT), micro computed tomography, and electron beam computed tomography (EBCT), and other imaging systems).

Figure 1:
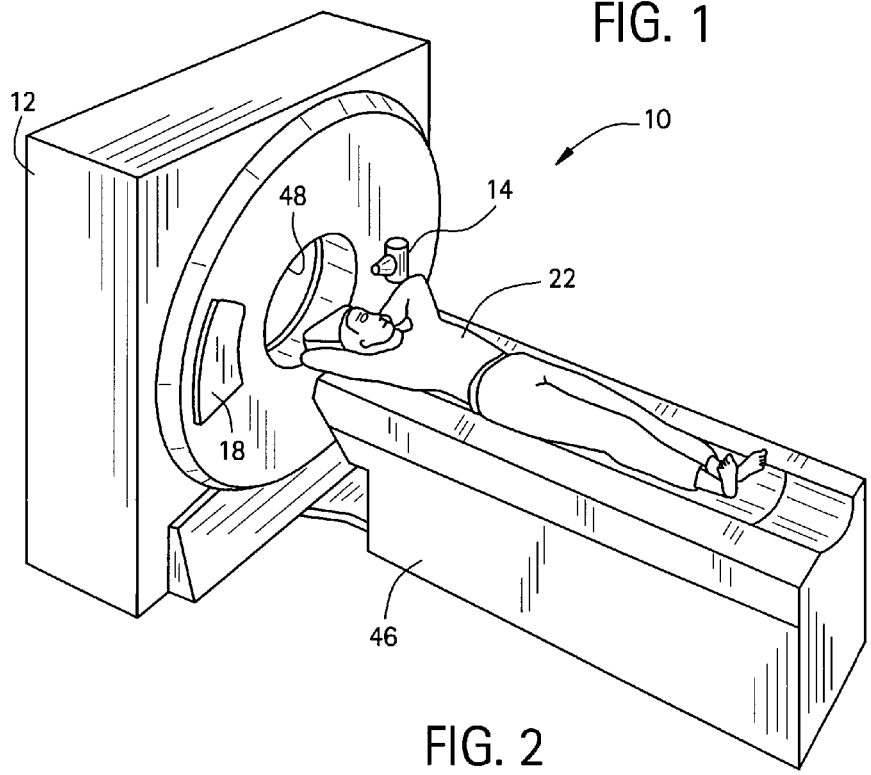
FIG. 1 illustrates a CT imaging system in accordance with an embodiment of the present invention.
Figure 2:
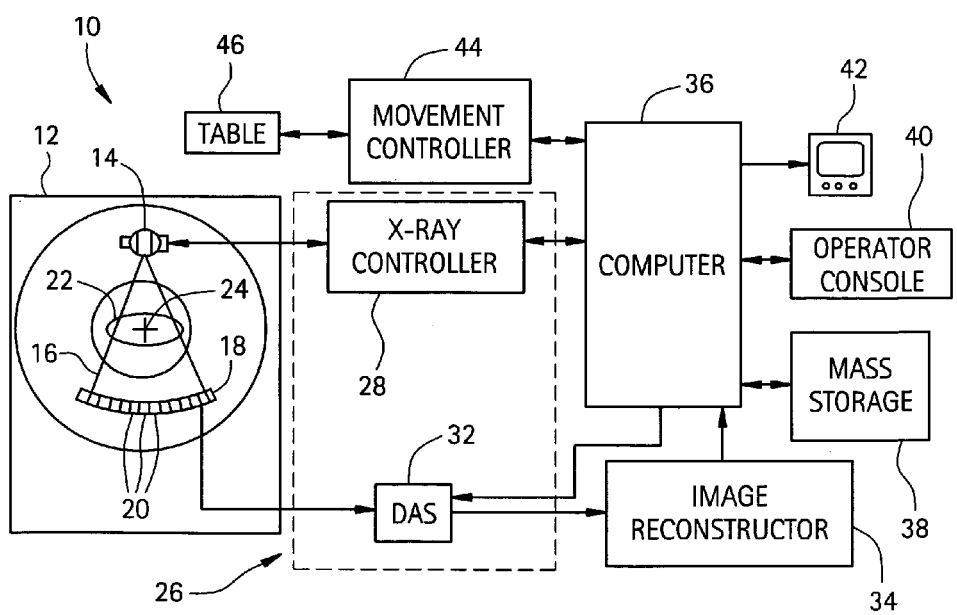
FIG. 2 illustrates a block diagram of a CT imaging system in accordance with an embodiment of the present invention.

FIG. 1 illustrates a CT imaging system 100 in accordance with an embodiment of the present invention. FIG. 2 illustrates a block diagram of a CT imaging system 200 in accordance with an embodiment of the present invention. FIGS. 1 and 2 illustrate embodiments of a CT imaging system as described in U.S. Pat. No. 6,385,292 to Dunham et al. X-rays from an x-ray source 14 may irradiate a patient 22 and impinge upon a detector 18. A data acquisition system (DAS) 32 may collect image data based on the x-rays impinging upon a detector 18. The DAS 32 may transmit image data to an image reconstructor 34. The image reconstructor 34 may form still and/or motion images from single and/or multiple slices of image data. The image reconstructor 34 may also use a computer 36 for image reconstruction, storage, and/or display.

The patient 22 is positioned in an object positioner 46. The object positioner 46 may be a table, a support, a wall bucky, or other movable or non-movable positioner, for example. The x-rays travels from the x-ray source 14 and impinge upon the detector array 18.

The detector array 18 includes at least one row of detector cells. The detector cells of the detector array 18 generate signals in response to the impinging x-rays. Each detector cell corresponds to a different channel. That is, a DAS channel may be mapped to a detector cell, for example. Each cell's signal may be described by a detector row, a detector channel, and a projection view of a signal.

The signals are transmitted from the detector array 18 to the DAS 32. The DAS 32 may be embodied in at least one of hardware and software. The DAS 32 collects the data, converts the analog signal to digital, and sends the data to the image reconstructor 34. The image reconstructor 34 analyzes the signals and generates a medical diagnostic image from the data obtained from the detector array 18. The image reconstructor 34 may also store data or transmit data to an external processor or memory, for example. The image reconstructor 34 may be embodied in software and/or in hardware, for example.

The DAS 32, the image reconstructor 34, and the computer 36 comprise an image processing system. The image processing system encompasses the abilities of the DAS 32 and the image reconstructor 34, including collecting the data and generating an image. In an embodiment, the computer 36 may be used to help process, storage, transmit, and/or display the image or image data. The components of the image processing system may be embodied in separate and/or combined units in hardware and/or in software.

The detector array 18 receives x-rays from several angles, along an arc concentric to the x-ray source, to produce a set of x-ray projections. Projection data is received by the DAS 32, and data from each detector row is arranged in a matrix called a sinogram. Within the sinogram, a row contains projection data for one view, and a column contains data for one detector cell. From a two-dimensional sinogram of projection data, the image reconstructor 34 may reconstruct a two-dimensional image in a step-and-shoot mode. For scan acquired in a helical mode, a sinogram from all detector rows is used to reconstruct a two-dimensional image. The two-dimensional image may characterize an axial slice of the object imaged, for example. The resulting image, however, may contain streaks or image artifacts due to imperfections or inaccuracies in the system 100.

A single failed DAS channel may introduce an error or an image artifact in a resulting image obtained using the system 100. An error or failure in an ASIC chip for the DAS 32 may induce a number of faulty channels. For example, a failed DAS ASIC may impact eight detector or DAS channels.

In an embodiment, the DAS 32 may include a capability of adjusting data to lessen occurrence of image artifacts. The DAS 32 may interpolate an estimate of a signal for a malfunctioning cell using good samples from the neighboring channels of the malfunctioning cell, in the same projection view and detector row as the malfunctioning cell. A good sample is a signal from a cell that is not malfunctioning. A good sample is in the same projection view as the malfunctioning cell. In an embodiment, a good sample is not in the same channel as the malfunctioning cell. The DAS 32 may then correct the interpolated estimate by adjusting the estimate. The estimate may be adjusted with a weighted average of a difference calculated using the same method of interpolation performed on neighboring rows. In an embodiment, the neighboring rows are at least one of the nearest pairs of neighboring detector rows. Each member of the pair is an equal distance above and below the detector row with the malfunctioning cell.

In an embodiment, at least one of the rows includes a good cell. A good cell contains a good signal in the same row position and projection view as the malfunctioning cell. A good signal comes from a cell that is not malfunctioning.

The error detected is calculated through differential signals measured in each row. The differential signal in each row is measured by subtracting a good cell's signal from the interpolation of the good cell's signal. The good cell's signal is estimated using the same method of interpolation used in estimating the signal of the malfunctioning cell, described above.

The weighted average of the differential signals may be weighted according to a variety of factors, such as a position of the rows in the array with respect to the middle of the array, a number of good signals in the rows with the good cell, a magnitude of the good cell's signal and the good cell's interpolated signal, a quality of the signals of the good cells, and similarities in measurements between the detector row with the malfunctioning cell and the neighboring detector rows with the good cells.

Alternatively, the interpolation may be applied to more than one neighboring pair of rows. The additional pairs of rows may be a next nearest pair of rows. Members of the pairs of rows may each be an equal distance above or below the detector row with the malfunctioning cell. At least one of the rows in the pair may include a good cell. If the pair of rows does not contain a good cell, a next nearest pair of rows may be considered. Differential signals are calculated using the method described above. A weighted average of the differential signals may be weighted according to a variety of factors, such as those listed above and including the number of rows between the row with the good cell and the row with the malfunctioning cell. Alternatively, outlier rows may be ignored in calculating the weighted average. Alternatively, statistical models may be used to calculate weights to be applied to each of the neighboring row's differential signal.

The DAS 32 may implement these steps through software inside a central processing unit of the DAS 32 and/or in a separate piece of hardware devoted to making the calculation of the signal of the malfunctioning cell, for example. Alternatively, the image reconstructor 34 and/or computer 36 may include a capability of adjusting the data to decrease the occurrence of image artifacts. The image reconstructor 34 may interpolate a signal of a malfunctioning cell using the same method of interpolation as above and correct an initial interpolation of the signal of the malfunctioning cell using the same method as above. The image reconstructor 34 may implement these steps through software inside a central processing unit of the image reconstructor 34 and/or in a separate piece of hardware devoted to making the calculation to estimate the signal, for example. Alternatively, hardware inside the detector array 18 or hardware associated with the detector array 18 may implement the signal correction before the signal is passed on to the DAS 32.

In an alternative embodiment, an output (not shown) may generate an alert based on the malfunctioning cell(s). The alert may be an alarm, a log, and/or a report, for example. The alert may inform an operator that a detector cell, detector or DAS channel, and/or a detector array should be repaired or replaced, for example.

Figure 3:
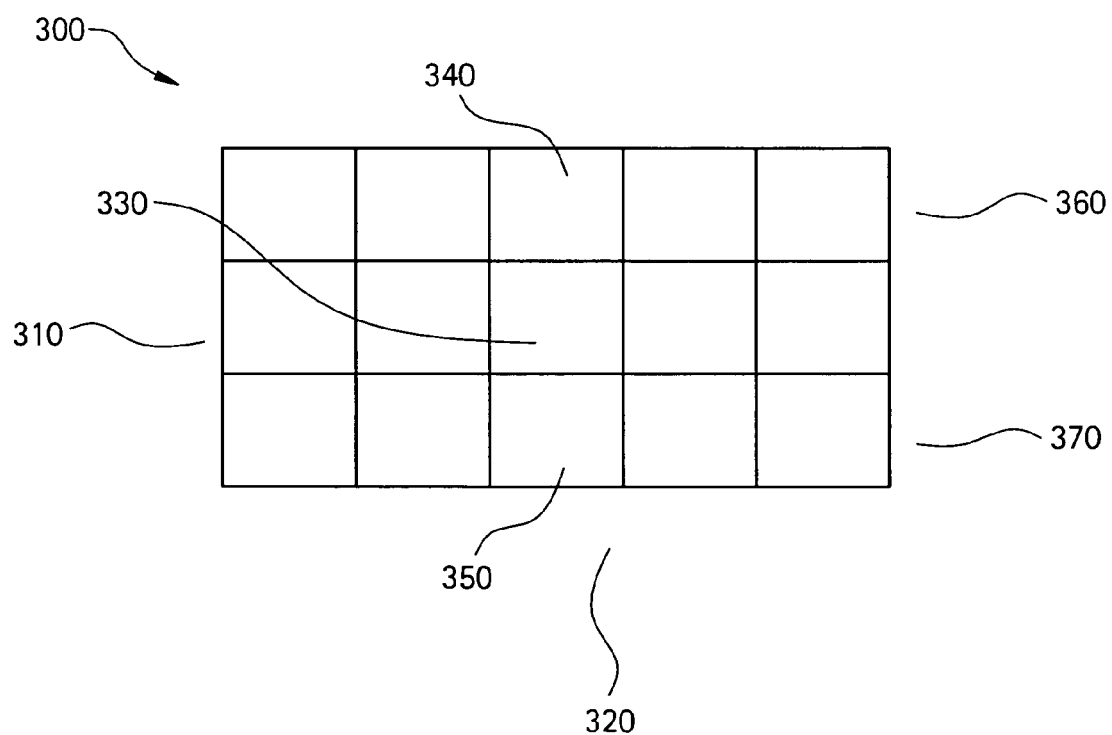
FIG. 3 shows a representation of an array of cells in projection view k illustrating the defective and non-defective sample locations used in accordance with an embodiment of the present invention.

FIG. 3 shows a representation of an array of cells 300 in a projection view k illustrating defective and non-defective sample locations in accordance with an embodiment of the present invention. The array of sample locations 300 includes a defective or malfunctioning cell (i, n) 330, a channel i 320, and a detector row n 310. The malfunctioning cell (i, n) 330 is located at the intersection of channel i 320 and detector row n 310. The malfunctioning cell 330 may not return an accurate signal. Surrounding cells may be utilized to estimate the malfunctioning cell's (i, n) 330 signal.

Figure 4:
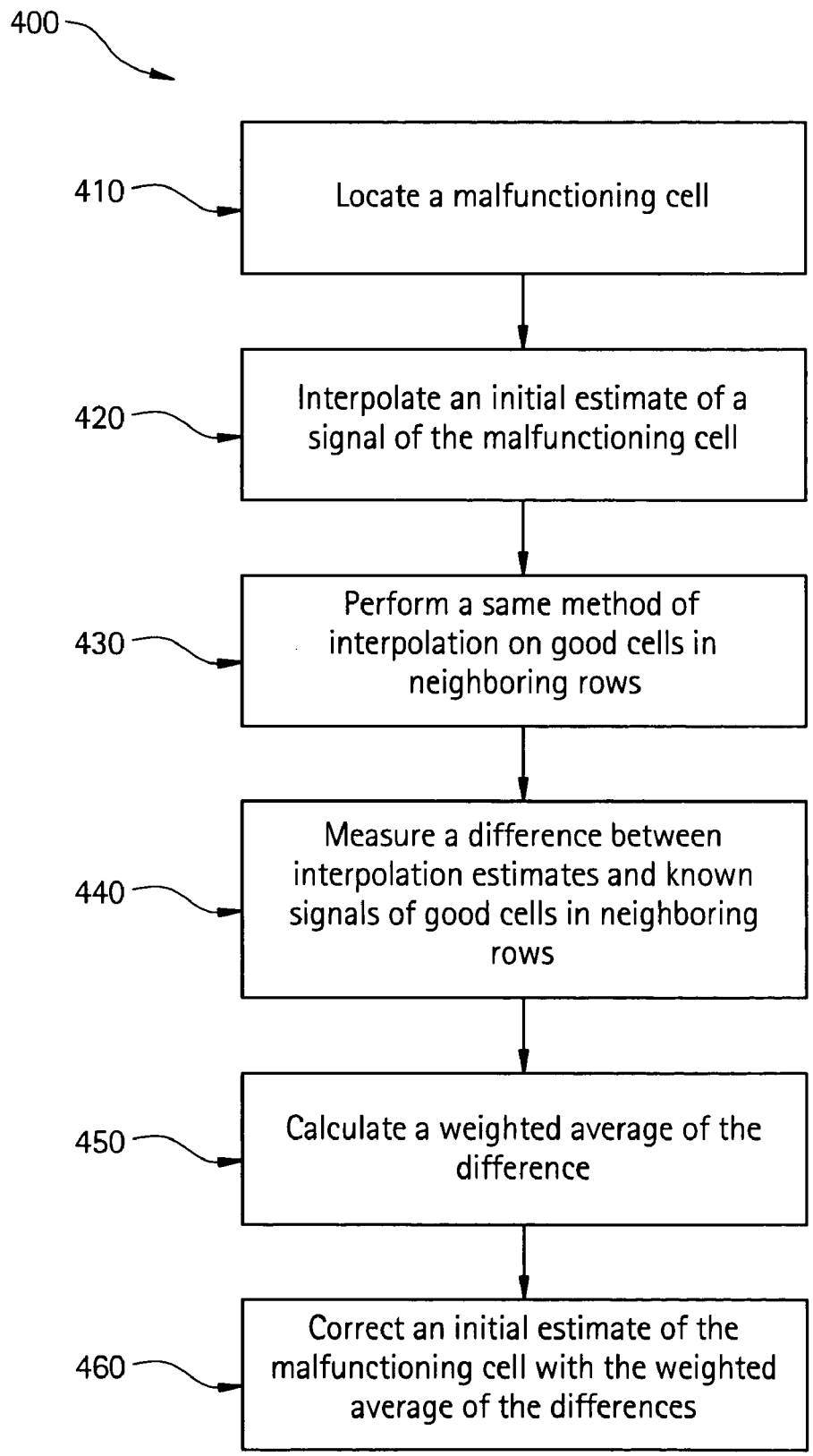
FIG. 4 shows a flow diagram for a method for estimating a missing projection sample in a projection view of a malfunctioning cell located in a detector row and a DAS channel in accordance with an embodiment of the present invention.

FIG. 4 shows a flow diagram for a method 400 for estimating a missing projection sample in a projection view of a malfunctioning cell 330 located in detector row 310 and channel 320 in accordance with an embodiment of the present invention. After a brief overview, the steps of a method for improved data acquisition will be described in further detail below. First, at step 410, at least one malfunctioning cell 330 is located. Then, at step 420, a signal of an initial estimate of the malfunctioning cell 330 is interpolated. Next, at step 430, a same method of interpolation is performed on neighboring rows 360, 370 with a good cell 340, 350. Then, at step 440, differences between the interpolation estimates and the signals of the good cells 340, 350 are measured. Next, at step 450, a weighted average of the differences is calculated. Finally, at step 460, the initial estimate of the malfunctioning cell 330 is corrected with the weighted average of the differences.

Now the method of improved data acquisition will be described in more detail. First, at step 410, at least one malfunctioning cell 330 is located. The malfunctioning cell 330 may be located using at least one of several methods, such as (1) exposing all cells in a detector array to x-rays and then comparing each cell's measurements to the cell's neighbors looking for variations between signals and (2) looking for changes in average signals (over all projection views for each channel) between adjacent cells which may identify malfunctioning cells.

The first approach is known as an air-calibration scan. In an embodiment, each imaging system undergoes a set of fast calibration process known as "air-cal". The air-cal process exposes detector cells directly to a beam of x-ray photons without any object in the beam. By examining differential readings obtained from neighboring detector cells 340, 350, a malfunctioning cell 330 is quickly identifiable. Over time, the malfunctioning cell 330 may function properly some of the time and improperly another part of the time. The malfunctioning cell 330 may be identified as a cell which is a set percentage below readings of neighboring cells 340, 350. The percentage may also vary according to the cell's location. For example, cells nearer to an ISO channel, a rotational center of a detector array 18, may be given a lower tolerance than other cells not near the channel. So a percentage difference threshold for the cells nearer to an ISO channel may be lower than those of cells not as near to an ISO channel.

A second approach used to identify the malfunctioning cell is through a use of patient scan data. The second approach's advantage is that not all hospitals or operators of imaging systems perform daily air-cals. Therefore, if an error is introduced in a detector cell between air-cal scans, the detector cell may not be properly identified. By using an average reading (over all projection views for each channel, for example), a comparison of average signals between adjacent cells may identify malfunctioning cells 330. Averaging projection views of detector cells may keep readings for each signal close to one another unless a cell is malfunctioning.

Both the air cal approach and the patient scan data approach may be implemented by a separate piece of hardware or software located in a variety of locations, such as the detector array 18, the DAS 32, the image reconstructor 34, and the computer 36. Degradation of the detector array 18 over time may be examined. Each time checks are performed to identify malfunctioning cells 330, changes in cell readings may be stored. Changes in cell readings may be examined to look for significant changes in the detector array 18. Changes may be identified, thus identifying malfunctioning cells 330 and potentially a detector array 18 or probe to be replaced. A log may be kept of all detected variations which surpass a set threshold, thus identifying malfunctioning cells 330. The log may be kept by a separate piece of hardware or software located a variety of locations, such as the detector array 18, the DAS 32, the image reconstructor 34, and the computer 36 or in a pre-existing piece of hardware utilized in the imaging system 100, for example. An alert or alarm may also be triggering to alert an operator or technician, for example.

Then, at step 420, an initial estimate, $p'_k(i, n)$, for the signal of malfunctioning cell (i, n) 330 is calculated via interpolation. Good samples are used from the same projection view and same detector row n 310 as malfunctioning cell (i, n) 330 but a different channel than channel i 320.

In an embodiment, the good samples are within a certain number of channels, M, around the channel i 320. In an embodiment, the certain number of channels, M, includes at least two good samples. Each good sample in neighboring channels of the malfunctioning cell (i, n) 330 is summed with each signal having been multiplied by an interpolation coefficient. A good sample contains a known, measured signal, which is not defective. The aforementioned step is embodied in the following equation:

$$p'_k(i, n) = \sum_{m=-M}^{-1} w_m p_k(i+m, n) + \sum_{m=1}^{M} w_m p_k(i+m, n). \quad (1)$$

The variable $W_m$ represents the interpolation coefficient. The value M is a set number of channels of at least 1. M may vary. M may be calculated dynamically so as to lessen the differential signals measured as discussed below. The interpolation coefficient may be a coefficient for a variety of interpolation techniques, such as a $4^{th}$ order Lagrange interpolator and cubic spline. If any neighboring channels are also malfunctioning, then the malfunctioning channel may be disregarded in the calculation.

Next, at step 430, a same method of interpolation, as used in step 420, is performed on at least one pair of neighboring detector rows 360, 370. In an embodiment, each neighboring row 360, 370 used is an equal number of rows above or below the detector row n 310. Signals $P_k(i, n-1)$ and $P_k(i, n+1)$ are in channel i 320 and detector rows n−1 and n+1, respectively. An estimation is performed using the same method of interpolation as was used in estimating $p'_k(i, n)$, to form estimate signals $p'_k(i, n-1)$ and $p'_k(i, n+1)$. The cells $p_k(i, n-1)$ and $p_k(i, n+1)$ are good cells 240, 250. At step 430, each signal of a good sample in a neighboring row 360, 370 with a good cell 340, 350 in the same projection view as the malfunctioning cell 330 is multiplied by an interpolation coefficient. Each signal multiplied by an interpolation coefficient is summed in the same manner as was discussed in step 420. In an embodiment, good samples are within the same number of channels, M, from the channel i 320. A good sample is a known, measured sample. If however, one of the samples from cells $p_k(i, n-1)$ and $p_k(i, n+1)$ is not known or is known or determined to be malfunctioning, then the unknown cell's row may not be considered. Thus, the neighboring row 360, 370 with a malfunctioning cell 330 in the place of a good cell 340, 350 is given a weight of zero in calculating the weighted average. If both cells $p_k(i, n-1)$ and $p_k(i, n+1)$ are known to be malfunctioning or are unknown, then step 430 performs the same steps on the next closest pair of rows 360, 370 with at least one good cell 340, 350.

The following equations may be used in step 430:

$$p'_k(i, n-1) = \sum_{m=-M}^{-1} w_m p_k(i+m, n-1) + \sum_{m=1}^{M} w_m p_k(i+m, n-1), \quad (2)$$

$$p'_k(i, n+1) = \sum_{m=-M}^{-1} w_m p_k(i+m, n+1) + \sum_{m=1}^{M} w_m p_k(i+m, n+1). \quad (3)$$

Variable $W_m$ represents the interpolation coefficient and value M is a set number of channels of at least 1. Alternatively, more than two rows 360, 370 may be considered in performing the same method of interpolation as the initial estimate on the neighboring rows 360, 370. The next nearest pairs of rows 360, 370 with at least one good cell 340, 350 may also be considered. The additional rows may go through the same steps as the rows 360, 370 with cells $p_k(i, n-1)$ and $p_k(i, n+1)$ go through. The steps include interpolating an estimate for a good cell's signal and calculating the differential signals between the good cell's measured signal and the good cell's estimated signal. The differential signals may then be weighted inversely proportional to the number of rows between the row 360, 370 with the good cell 340, 350 and the row 310 with the malfunctioning cell 330. Additionally, other factors may be considered in weighting an average of differential signals, as described below.

Next, at step 440, differential signals, $\Delta_k(i, n-1)$ and $\Delta_k(i, n+1)$, are calculated as the difference between the measured projection signals, $p_k(i, n-1)$ and $p_k(i, n+1)$, and the estimated signals, $p'_k(i, n-1)$ and $p'_k(i, n+1)$. The following equations indicate how $\Delta_k(i, n-1)$ and $\Delta_k(i, n+1)$ are calculated:

$$\Delta_k(i,n-1)=p'_k(i,n-1)-p_k(i,n-1) \quad (4),$$

$$\Delta_k(i,n+1)=p'_k(i,n+1)-p_k(i,n+1) \quad (5).$$

Due to the close proximity between detector rows n−1, n, and n+1, an additional adjustment to detector row n 310 is likely be similar to differentials detected of detector rows n−1 and n+1. The differential signals, $\Delta_k(i, n-1)$ and $\Delta_k(i, n+1)$, are used to calculate an additional adjustment needed to make $p'_k(i, n)$ into a more accurate estimation of the malfunctioning cell (i, n) 330.

Then, at step 450, a weighted average of the differential signals, $\Delta_k(i, n)$, is calculated. The weighted average $\Delta_k(i, n)$ is also the additional adjustment to the initial estimation $p'_k(i, n)$. The weighted average $\Delta_k(i, n)$ is calculated as shown in the following equation:

$$\Delta_k(i,n)=\alpha_1\Delta_k(i,n-1)+\alpha_2\Delta_k(i,n+1) \quad (6).$$

The weights, $\alpha_1$ and $\alpha_2$, may be calculated based on a variety of factors, such as a magnitude of the estimated signals, $p'_k(i, n-1)$, $p'_k(i, n)$ and $p'_k(i, n+1)$; a magnitude of the measured projection signals $p_k(i, n-1)$ and $p_k(i, n+1)$ of the neighboring rows 360, 370 with good cells 340, 350 used in the calculation; the position of the rows 360, 370 used in the calculation with respect to edges of the detector array 18; a number of good samples in the detector row n 310 and in the neighboring detector rows 360, 370 with the good cells 340, 350 used in the calculation; the quality of the good cells' signals; and the similarities in measurements between detector row n 310 and the neighboring detector rows 360, 370 with good cells 340, 350. The weights, $\alpha_1$ and $\alpha_2$, may be adjusted dynamically. In an embodiment $\alpha_1$ and $\alpha_2$ both equal one half.

Finally, at step 460, a final estimated projection signal, $p''_k(i, n)$, is calculated from the weighted average of the differential signals, $\Delta_k(i, n)$, subtracted from the initial estimate, $p'_k(i, n)$, as shown in the following equation:

$$p''_k(i,n)=p'_k(i,n)-\Delta_k(i,n) \quad (7).$$

The final estimated projection signal, $p''_k(i, n)$, is an estimate of the signal of the malfunctioning cell (i, n) 330 using other signals within the same projection view as the malfunctioning cell (i, n) 330.

Figure 5:
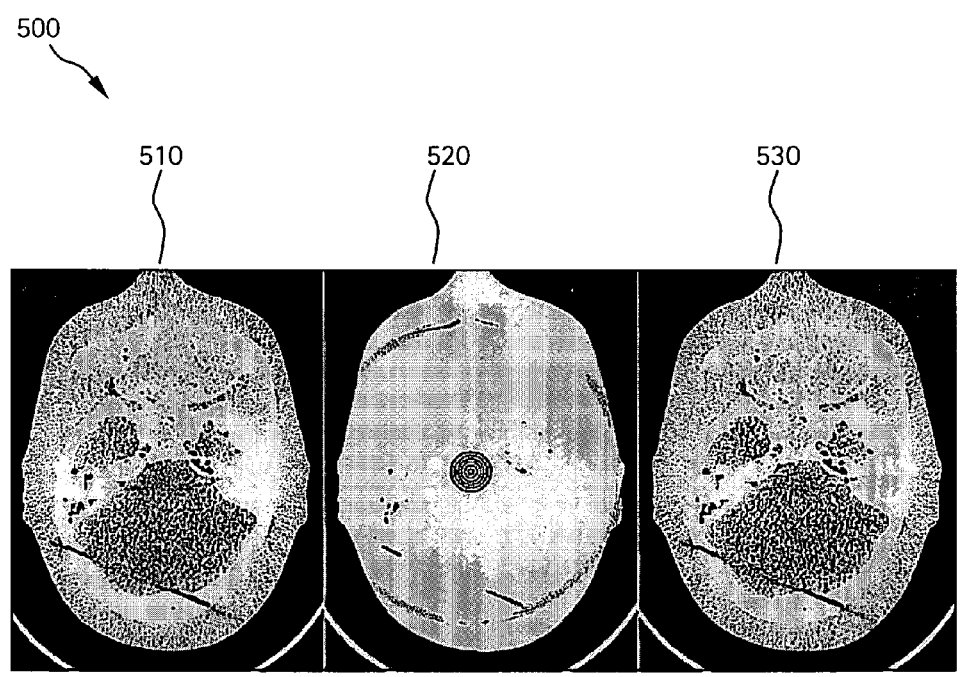
FIG. 5 depicts a human skull phantom scan to illustrate effectiveness of the proposed correction to the imaging system in accordance with an embodiment of the present invention.

FIG. 5 depicts a human skull phantom scan 500 to illustrate an example of effectiveness of the proposed correction to the imaging system 100 in accordance with an embodiment of the present invention. FIG. 5 includes a reconstructed good scan 510 collected on a good detector array 18, a bad scan 520 with malfunctioning channels and no correction, and a corrected scan 530 with malfunctioning channels and channel correction. In the good scan 510, no artifacts are observed. To simulate a malfunctioning channel effect in the bad scan 520, detector channel readings from multiple channels, for example, six channels in a detector array of 1000 channels, are set to zero. In the bad scan 520, severe image artifacts are observed. In the corrected scan 530, a correction is applied to the bad scan's corrupted projections, as described above, and image reconstruction is then performed. The corrected scan 530 shows a reconstructed image with a malfunctioning-channel correction, as described above. Compared to the good scan 510, the corrected scan's 530 artifacts are minimized.

Figure 6:
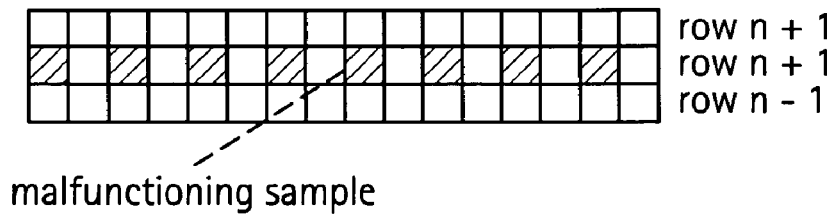
FIG. 6 shows an example of malfunctioning and non-malfunctioning sample locations in a DAS ASIC failure used in accordance with an embodiment of the present invention.

In an alternative embodiment, error correction may be implemented in an imaging system that includes a DAS ASIC to map to detector cells. FIG. 6 shows an example of malfunctioning and non-malfunctioning sample locations from a DAS ASIC failure in accordance with an embodiment of the present invention. Unlike in a detector failure, where a bad detector cell affects projection samples corresponding to the detector cell location, a malfunctioning DAS ASIC may impact multiple projection samples. For example, a DAS ASIC malfunction may affect projection samples corresponding to eight detector cells. Thus, in an embodiment, DAS channel mapping to a detector using a DAS ASIC optimizes performance for correction of malfunctioning channels or cells.

In an embodiment, as shown in FIG. 6, DAS ASICS are mapped to alternating detector cells in a detector row. Mapping to alternative cells may minimize banding in a resulting image due to malfunction in an ASIC. For example, a failure in a DAS ASIC produces a pattern of eight bad channels, every other detector cell, in a detector row. The bad channels produce eight rings in a single axial image.

Figure 7:
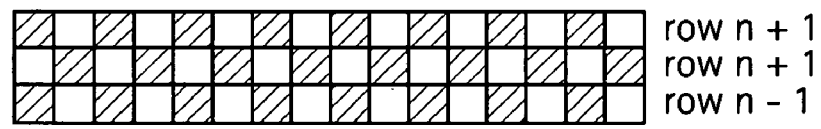
FIG. 7 depicts an example of DAS mapping with two ASICs used in accordance with an embodiment of the present invention.

As described in more detail above, a detector signal, $p_k(i$ n), may be estimated by performing linear or bilinear interpolation using neighboring signals. That is, $p_k(i, n)$ may be estimated using average signals of $p_k(i-1,n)$ and $p_k(i+1,n)$ for linear interpolation and $p_k(i-1,n)$, $p_k(i+1,n)$, $p_k(i,n-1)$, and $p_k(i,n+1)$ for bilinear interpolation. FIG. 7 depicts an example of a DAS mapping with two ASICs used in accordance with an embodiment of the present invention. As shown in FIG. 7, a DAS ASIC does not sample two detector channels that are adjacent to each other.

Figure 8:
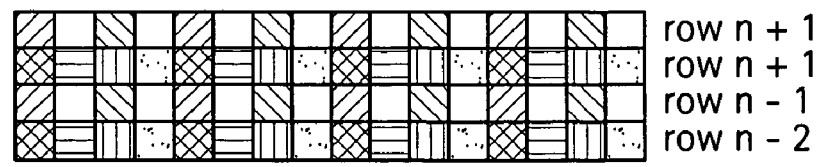
FIG. 8 illustrates an example of a DAS ASIC mapping with eight ASICs used in accordance with an embodiment of the present invention.

Alternatively, signal correction may be performed in two iterations. In the first iteration, a malfunctioning channel is estimated using neighboring good channels of the same row. Similar operations are performed on adjacent detector rows (for example, on both sides of the malfunctioning channel or on one side and the current row). A difference between estimated and real measurements of good detector rows is used to further refine the bad channel estimation in the second iteration. FIG. 8 illustrates an example of a DAS ASIC mapping with eight ASICs used in accordance with an embodiment of the present invention.

Thus, certain embodiments of the present invention provide a method and system for minimizing an impact of a defective detector cell or DAS channel by minimizing visible artifacts which may be observed. The system and method improve the accuracy and availability of images displayed to an observer by limiting an interpolation of a signal for a malfunctioning cell to other good signals within the same projection view. Certain embodiments minimize an impact of a failed detector or DAS channel on imaging or system performance. Certain embodiments also allow detection of bad channel(s) to facilitate proper maintenance and reliability of an imaging system.

While the invention has been described with reference to certain embodiments, it will be understood by those skilled in the art that various changes may be made and equivalents may be substituted without departing from the scope of the invention. In addition, many modifications may be made to adapt a particular situation or material to the teachings of the invention without departing from its scope. Therefore, it is intended that the invention not be limited to the particular embodiment disclosed, but that the invention will include all embodiments falling within the scope of the appended claims.

The invention claimed is:

1. A method for improved image data acquisition, the method comprising:
   forming an initial estimate of a malfunctioning cell in an array of detector rows using cells in a same detector row and projection view as the malfunctioning cell, wherein a detector cell is located in a detector row containing multiple channels; and
   adjusting the initial estimate according to an accuracy of estimates performed on at least one of a nearest pair of neighboring detector rows, wherein each member of the pair of rows is an equal distance above or below the detector row with the malfunctioning cell, wherein at least one of the members has a good cell.

2. The method of claim 1, wherein the initial estimate comprises an interpolation of a signal of the malfunctioning cell.

3. The method of claim 2, wherein the interpolation comprises summing a product of interpolation coefficients and signals of channels of cells in the same detector row and projection view as the malfunctioning cell.

4. A method for improved image data acquisition, the method comprising:
   forming an initial estimate of a malfunctioning cell in an array of detector rows using cells in a same detector row and projection view as the malfunctioning cell, wherein a detector cell is located in a detector row containing multiple channels; and
   adjusting the initial estimate according to an accuracy of estimates performed on at least one of a nearest pair of neighboring detector rows, wherein each member of the pair of rows is an equal distance above or below the detector row with the malfunctioning cell, wherein at least one of the members has a good cell, and
   wherein said adjusting step further comprises calculating a weighted average of estimates from the pairs of rows.

5. The method of claim 4, wherein said step of calculating a weighted average further comprises calculating the weighted average according to magnitudes of the initial estimate and measurements in the neighboring detector rows.

6. The method of claim 4, wherein said step of calculating a weighted average further comprise calculating the weighted average according to magnitudes of measured signals of good cells in the pair of rows above and below the detector row with the malfunctioning cell.

7. The method of claim 4, wherein said step of calculating a weighted average further comprises weighting the estimate of a neighboring row as zero for a neighboring row without a good cell.

8. The method of claim 4, wherein said step of calculating a weighted average further comprises assigning a greater weight to the estimate of a good cell's signal in the detector row closer to an ISO row of the array.

9. The method of claim 4, wherein said step of calculating a weighted average further comprises calculating the weighted average according to quality of the signals of the good cells.

10. The method of claim 4, wherein said step of calculating a weighted average further comprises assigning a greater weight to a neighboring detector row with a good cell signal with a closer measurement to the initial estimate of the malfunctioning cell.

11. The method of claim 4, wherein said step of calculating a weighted average further comprises calculating the weighted average according to similarities between the neighboring detector rows with the good cells and the detector row of the malfunctioning cell.

12. A method for error detection in an image detector array, the method comprising:
    exposing detector cells directly to an x-ray beam without an object to be imaged in the x-ray beam; and
    comparing average readings between adjacent cells over all projection views for a channel to identify one or more malfunctioning cells;
    wherein said step of comparing comprises measuring a difference between a first reading from a detector cell and at least second and third readings from neighboring cells; and
    using the difference between the first, second, and third readings to identify a malfunctioning cell.

13. The method of claim 12, further comprising storing a position of the malfunctioning cell.

14. The method of claim 12, further comprising generating an alert identifying the one or more malfunctioning cells.

15. An imaging system with improved error correction, said system comprising:
    an image detector array; and
    an image processing system, wherein the image processing system interpolates a signal of a known malfunctioning cell in the image detector array in a projection view using a method of interpolation, wherein the image processing system adjusts the signal based on a weighted average of first and second difference signals produced using the method of interpolation with at least two neighboring rows in the image detector array in the projection view.

16. The imaging system of claim 15, wherein the weighted average is based on at least one of signal magnitude, signal quality, and row location in the image detector array.

17. The imaging system of claim 15, further comprising an output capable of generating an alert for the malfunctioning cell.

18. The imaging system of claim 15, wherein the image processing system comprises at least one of a reconstruction system and a data acquisition system.

19. The imaging system of claim 15, wherein the image detector array uses the projection view to interpolate the signal of the known malfunctioning cell in the image detector array, and adjusts the signal based on a weighted average of first and second difference signals produced using the method of interpolation with at least two neighboring rows in the image detector array in the projection view.

20. A method for reducing errors in image data acquisition, said method comprising:

examining at least one of a cell or an application-specific integrated circuit (ASIC) in an imaging system;

mapping the ASIC to optimize opportunities for error correction;

identifying at least one of a malfunctioning channel and a malfunctioning ASIC; and applying a correction scheme to reduce an error due to the at least one of a malfunctioning channel and a malfunctioning ASIC.

21. The method of claim 20, further comprising:

estimating a value of the at least one of a malfunctioning channel and a malfunctioning ASIC;

performing a same estimation on rows adjacent to a row including a cell connected to the at least one of a malfunctioning channel and a malfunctioning ASIC; and using a difference between said estimating and said performing steps to refine said value.

* * * * *

UNITED STATES PATENT AND TRADEMARK OFFICE
CERTIFICATE OF CORRECTION

PATENT NO. : 7,142,636 B2
APPLICATION NO. : 10/668444
DATED : November 28, 2006
INVENTOR(S) : Jiang Hsieh et al.

It is certified that error appears in the above-identified patent and that said Letters Patent is hereby corrected as shown below:

On the title page, item "(75) Inventors:" please add the following inventor names:

--Gary R. Strong, Waukesha, WI;
Willi Walter Hampel, Harland, WI;
Koji Bessho, Tokyo, Japan--.

In col. 8, line 45, delete "$W_m$" and insert --$w_m$--.

In col. 8, line 58, after the word "Signals", please delete "$P_k$" and insert --$p_k$--.

In col. 8, line 58, after the word "and", please delete "$P_k$" and insert --$p_k$--.

In col. 8, line 63, delete "$P_k(i$" and insert --$p_k(i,$--.

In col. 9, line 25, delete "$W_m$" and insert --$w_m$--.

Signed and Sealed this

Thirtieth Day of March, 2010

David J. Kappos
*Director of the United States Patent and Trademark Office*